United States Patent [19]

Williamson

[11] Patent Number: 5,047,427

[45] Date of Patent: Sep. 10, 1991

[54] TREATMENT FOR SECONDARY DIABETES EFFECTS

[75] Inventor: Joseph R. Williamson, St. Louis, Mo.

[73] Assignee: Washington University, St. Louis, Mo.

[21] Appl. No.: 264,589

[22] Filed: Oct. 31, 1988

[51] Int. Cl.⁵ .......................................... H61K 31/19
[52] U.S. Cl. .................................................. 514/557
[58] Field of Search ...................................... 514/557

[56] References Cited

PUBLICATIONS

Gonzalez et al., (1986), Diabetes, 35:1200–1205.
Varma et al., (1974), Biochim. Biopys. Acta, 338:632–640.
Greene et al., (1985), Diabetes Care 8, (3):290–299.
Travis et al., The Journal of Clinical Investigation, (1971), 50:2104–2112.
McLean et al., Diabetic Medicine, (1978), 2:189–193.
Goheen et al., Lipids, (1981), 16:1:43–51.
Stanko et al., Metabolism, (1986), 35:2:182–186.
Stanko et al., J. Lab. Clin. Med., (1978), 91:2:228–235.
Williamson, Abstract for 1988 Meeting of the American Diabetes Association, Inc.
Kinoshita et al., (1979), Metabolism 28, suppl. 1., pp. 462–469.
Tilton et al., (1988), Investigative Opthalmology and Visual Science, 29(6):861–868.
Williamson et al., (1988), Diabetes/Metabolism Reviews, 4(4)339–370.

Primary Examiner—Jerome D. Goldberg
Attorney, Agent, or Firm—Irell & Manella

[57] ABSTRACT

The invention provides a method to ameliorate or prevent the secondary damaging effects of diabetes by affecting oxidation of sorbitol in insulin-independent cells. Pyruvate salts and/or NAD⁺ precursors administered in a repetitive protocol provide protection against these secondary effects.

5 Claims, 2 Drawing Sheets

TREATMENT FOR SECONDARY DIABETES EFFECTS

TECHNICAL FIELD

The invention relates to the field of vascular complications of diabetes. Specifically, it concerns medications which can be administered as dietary supplements to prevent and control the secondary vascular effects of diabetes.

BACKGROUND ART

It is well understood that diabetes is a symptomology whose primary cause is a deficiency in the supply of insulin. Two major types of diabetes are recognized---childhood-onset diabetes, which is characterized by the absence of functional beta cells normally responsible for insulin secretion from the islets of Langerhans, and adult-onset diabetes, which is characterized by a progressive debilitation of functional beta cells. The primary treatment for diabetes is, in any case, seeing to the supply of insulin in the subject, either by directly supplying animal or human insulin orally or by injection or, in the case of adult-onset diabetes, alternative or additional administration of agents, such as glyburide or tolbutamide, which stimulate the secretion of insulin by the indigenous cells.

Whatever the primary treatment regimen, it is difficult or impossible to duplicate the fine-tuned regulation of glucose metabolism mediated by endogenous insulin in the normal person. There will be periods of unduly elevated insulin levels which may lead to insulin shock or hypoglycemia, and other periods when insulin levels are too low, associated with high circulating levels of glucose in the plasma. It is, at least indirectly, these elevated circulating glucose levels which are responsible for the secondary complications of diabetes, including deterioration of the lens and retina, vascular damage leading to increases in blood flow and albumin penetration of the blood vessels, and abnormalities in the red blood cells. These deleterious effects result because the affected tissues are able to take up glucose independent of insulin, a capability not possessed by fat cells and most muscle cells. Because insulin is lacking, high levels of circulating glucose are available for easy entry into cells lacking this control mechanism.

It is also understood that the normal metabolic pathway for glucose in these noninsulin-regulated cells involves conversion by the glycolytic pathway for energy production. Glycolysis is known to proceed only when adequate levels of $NAD^+$ are present. However, when glucose uptake levels are excessive, a large portion of the glucose is converted to sorbitol in a reaction catalyzed by aldose reductase, an enzyme whose cofactor is NADPH. The formation of sorbitol in large quantity reduces the availability of $NAD^+$, because it serves as a hydrogen acceptor during the oxidation of sorbitol to fructose by sorbitol dehydrogenase and is thus converted to NADH.

Prevention of the deleterious effects of sorbitol by administration of inhibitors of aldose reductase is well known. A number of simple synthetic compounds which are capable of inhibiting this enzyme are currently being used or are under development. These compounds prevent the formation of the sorbitol substrate, which would otherwise deplete $NAD^+$ when converted to fructose, and the resulting effects of $NAD^+$ depletion on glycolysis. For example, MacLean, P., et al, *Diabetic Med* (1978) 2:189-193 demonstrate the effect of sorbinil on the levels of various carbohydrate metabolites in diabetic rat lens, and conclude that the aldose reductase pathway is interconnected with, e g., glycolysis by virtue of its effect on $NAD^+$/NADH. These inhibitors, while putatively efficacious, are foreign compounds which have the potential for serious side effects.

Travis, S.F., et al, *J. Clin Invest* (1971) 50:2104-2112 studied the effect of elevated glucose concentrations on human erythrocytes. It was found that addition of pyruvate to the medium prevented the accumulation of "total triose phosphates" which otherwise occured. Addition pf pyruvate presumably affects the abnormal lactate/pyruvate ratio in these cells.

The invention provides an alternative approach to the prevention of secondary diabetes symptoms which involves the administration only of natural metabolites, preferably by mouth, and in dosage forms usable as dietary supplements. These metabolites, rather than preventing the formation of sorbitol, counteract the consequences of its subsequent metabolism to fructose.

DISCLOSURE OF THE INVENTION

The invention provides dietary supplements which are capable of preventing the secondary effects of diabetes in cells characterized by glucose uptake mechanisms which are not regulated by insulin. It has been found that by administering pyruvate salts and/or nicotinic acid or nicotinamide, the depletion of $NAD^+$ reserves by sorbitol can be prevented or reduced, and the otherwise resultant tissue damage ameliorated.

Thus, in one aspect, the invention is directed to a method to prevent or reduce the secondary effects of diabetes in a diabetic subject, which method comprises administering to the diabetic an amount of agent capable of elevating $NAD^+$ levels, such as pyruvate salts and/or nicotinic acid or nicotinamide, effective to prevent or reduce damage to tissues due to the effects of enhanced glucose uptake. In another aspect, the invention is directed to formulations for administering these active ingredients.

MODES OF CARRYING OUT THE INVENTION

Figure 1:
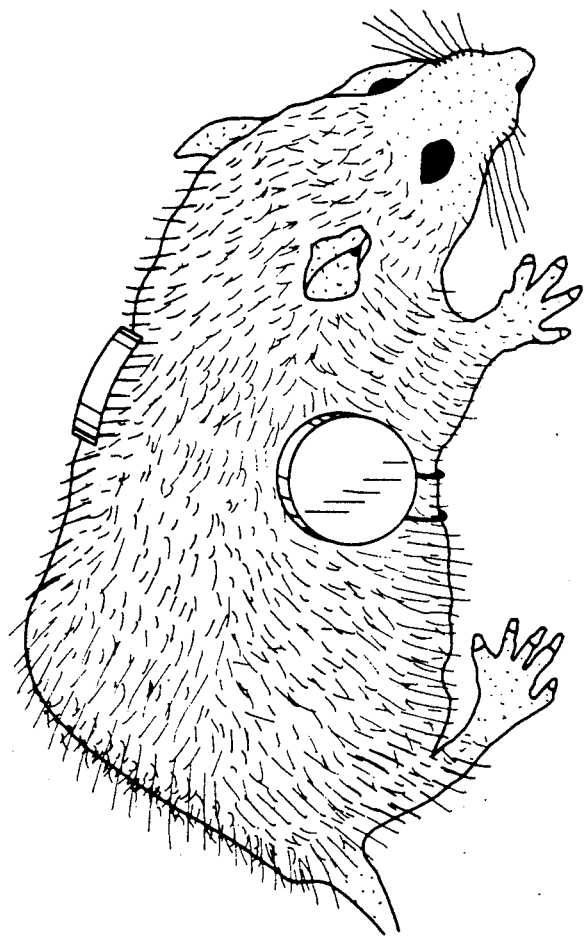
FIG. 1 shows the model system for measuring the effect of administered supplements.

The subjects who will benefit from the dietary supplements and medicaments of the invention are diabetics. During treatment according to the method of the invention, these diabetics will maintain, in more or less intact form, their previous regimen with respect to insulin stimulation or administration. While the benefits of the substances administered according to the invention may somewhat lower the insulin requirements due to mitigation of the side effects of insulin deficiency in general, an insulin administration protocol must continue to be observed in order to maintain the capability of insulin-dependent cells to take up the glucose needed for their energy-producing metabolism. Thus, the subjects for the method of the invention are diabetics more or less maintaining their normal protocols to assure insulin supply.

The substances employed in the method of the invention to prevent secondary tissue damage in diabetics fall into two major categories. The first category is pyruvate salts; the second major category is precursors of NAD+, typically nicotinamide or nicotinic acid. Both of these materials are compounds normally found in humans, and thus are relatively devoid of undesirable side effects.

Pyruvate is a committed metabolite at the end of the glycolytic pathway. Under anaerobic conditions it is reduced to lactate; under aerobic conditions, as in actively metabolizing muscle cells containing mitochondria and their attendant electron transport chain, it is mobilized into the citric acid cycle and completely oxidized to carbon dioxide.

The reduction of pyruvate to lactate increases the ratio of NAD+/NADH which is favorable to oxidation of glyceraldehyde-3-phosphate by the enzyme G-3-P dehydrogenase. Since the oxidation of glyceraldehyde-3-phosphate and of sorbitol both require NAD+ as a hydrogen acceptor, if sorbitol levels rise because of increased glucose levels, the availability of NAD+ becomes rate limiting to the oxidation of both substrates. Providing cells with exogenous pyruvate permits them to reduce the pyruvate to lactate while simultaneously oxidizing NADH to NAD+ by the enzyme lactate dehydrogenase.

It is evident that any oxidizing agent which is effective in converting NADH to NAD+ would be potentially effective in offsetting the effects of sorbitol oxidation in a similar manner. However, the presence of lactate dehydrogenase in the target cells, which catalyzes the transfer of electrons from NADH to pyruvate, makes pyruvate a convenient choice.

This approach should be contrasted to the studies of Stanko, R.T., et al, *J Lab Clin Med* (1978) 91:228–235; Stanko, R.T., et al, *Metabolism* (1986) 35:182–186; and Goheen, S.C., et al, *Lipids* (1981) 16:43–51. In these studies, rats were fed a diet supplemented with dihydroxyacetone (DHA), pyruvate, and riboflavin in order to suppress the accumulation of fat in liver cells. In particular, these supplements inhibited the build-up of fats in the liver when alcohol was administered to rats as a significant part of the diet. Whatever the mechanism of the effects of this dietary supplementation, they are different from that of the herein invention. The indicators of secondary damage, measured as described in the examples set forth below, permit the assessment of the effect of pyruvate in counteracting the effects of sorbitol. Assessment of these indicators in the presence and absence of pyruvate, and with and without supplementation of the pyruvate with dihydroxyacetone, shows that the effects of pyruvate in this system are reversed by the concomitant administration of DHA as described by Stanko. In particular, an enhanced sorbitol level is obtained when DHA is coadministered. This is thought to be due to the position of DHA in the glycolytic pathway, at which the progress of glycolysis is reversible. DHA (after phosphorylation) is, in fact, capable of recondensation with glyceraldehyde-3-phosphate to form fructose.

In the method of the invention, the pyruvate is administered to the subject at a level of about 10–100 g/day, preferably 25–35 g/day, measured as the pyruvate residue. Pyruvic acid per se cannot be administered because it is too acidic; therefore, the salt form must be used. Potentially suitable salts include the soluble salts of inorganic cations such as sodium, potassium, magnesium, or calcium. The sodium salt, although readily available, is not preferred as the major source of pyruvate because of its potential to upset the salt balance of the subject. The calcium salt is commercially available, and is advantageous as it simultaneously supplies a source of additional calcium. This can be of particular importance in individuals who require calcium supplementation in their diets. The pyruvate salts may also be salts of pharmaceutically acceptable organic residues, such as caffeine.

In order to balance the desired quantities of pyruvate anion and counterbalancing cation of a particular description, mixtures of various salts can be used. One particularly advantageous salt is the salt formed with nicotinamide, a NAD precursor discussed below. As the dosage requirements for nicotinamide are substantially less than those for pyruvate, typically only a portion of the pyruvate administered will be in the form of the nicotinamide salt.

The administration of pyruvate salts is effective in attaining the desired levels of pyruvate in the cells, as pyruvate is utilized in nonphosphorylated form. Pyruvate thus readily enters cells, and no mechanism for its subsequent phosphorylation is required. Other metabolites normally occurring in the glycolytic pathway, such as phosphoenylpyruvate, are not convenient as the phosphorylated forms of these compounds will not enter the cell.

The pyruvate salts may be formulated as solutions or dispersions in liquid for oral administration. The formulation will typically include flavoring elements. Thus, for example, the appropriate amount of the pyruvate salt may be mixed into orange juice, lemonade, chocolate drink, and the like. Typically, the dosage will be administered in several portions during the day, the precise regimen depending on the subject's insulin-administration and eating habits, the severity and timing of the fluctuation of glucose in the subject's blood stream, and the assessment of the attending physician. In general, the pyruvate will be administered slightly in advance of the anticipated peak of circulating glucose levels. This will generally occur several hours after the administration of insulin or insulin stimulator, and after ingestion of glucose-generating foodstuffs. In a typical regime, which is exemplary but not limiting, the subject might ingest one-third of the daily dose approximately one-half hour before breakfast, another third one-half hour before lunch, and the remaining third about one-half hour before dinner. The optimal protocol for each subject must be determined individually, as is presently the case with respect to protocols for insulin administration.

Besides pyruvate salts, the other major class of compounds suitable to the method of the invention comprises precursors of NAD+. The most convenient forms of precursors are nicotinic acid and nicotinamide, which are common dietary supplements also known as niacin and niacinamide. The effects of these precursors is evidently to enhance the supply of NAD+, thus permitting increased oxidation of sorbitol to fructose without depletion of the required reserves of NAD+ needed by the cell for glycolysis and other essential synthetic activities. Nicotinic acid, like pyruvate, should be administered as the salt in order to prevent excess acidity; however, as smaller amounts are required, this is not a requirement if the dosage is sufficiently low. However, suitable salts are those of inorganic ions such as sodium, potassium, and calcium, or other pharmaceutically acceptable organic cations. Nicotinic acid or niacin may also be administered as acid addition salts with inorganic acids such as the hydrochloride or sulfate, or with pharmaceutically acceptable anions such as acetate, citrate, and the like. A particularly favored organic counter-ion is pyruvate, as this supplies an additional substance useful in the method of the invention as described above. The quantity of niacin or nicotinic acid required is on the order of 1-3 g/day.

As the requirement for the precursor is relatively less than that for pyruvate, it can be supplied orally either in tablet form or, as described for pyruvate, as a supplement to a beverage. The protocols and timing of administration are similar to those described above for pyruvate.

It will be immediately apparent that treatment with pyruvate and NAD+ precursors is not mutually exclusive, and protocols involving the administration of either or both of these supplements are within the scope of the invention. If both pyruvate and precursor are utilized, they can be administered simultaneously, in part as portions of the same salt. In addition, regimes which involve administration of pyruvate and precursor on alternate days or on alternate sets of days, or on alternate periods during a single day, are also within the scope of the method.

It will also be evident that while the administration of the pyruvate or precursor active ingredients has been described using oral administration as a model, there is no theoretical reason why other modes of administration could not be used, including injection, nasal administration, and administration via suppository. However, when oral administration is possible, it is generally preferred. In some cases, the subject, because of other debilitations, may be unable to ingest materials by mouth. In these instances, as in the case of seriously ill patients, for example, intravenous administration or administration by injection generally, can also be used. Suitable adjustment of the dosage regime to accommodate these alternate modes of administration is well understood in the art.

The following examples are intended to illustrate, but not to limit, the invention.

EXAMPLE 1

Animal Model for Glucose Metabolism Effects

An animal tissue-specific, nonsystemic model was used to test the effects of various substances on the secondary symptomology of diabetes. In this animal model, bilateral skin chambers were mounted on normal Sprague-Dawley male rats after removing a two-centimeter circle of skin to induce granulation tissue formation. This permits introduction of materials into each chamber and examination of the effect of these materials on the tissue exposed. The experimental system with chambers in place is illustrated in FIG. 1.

In one assay, seven rats were implanted with the dual chambers. After ten days, 0.5 ml of 30 mM D-glucose in PBS plus 0.5% BSA plus 2% polyvinylpyrollidone was added to one chamber on each rat two times daily for ten days to simulate the high glucose levels characteristic of diabetes. Using the same regimen, 0.5 ml of 30 mM L-glucose (which is not metabolized) in a similar aqueous system was added to the other chamber as a control. The rats were then anesthetized with Inactin (100 mg/kg) and the blood flow and albumin permeation were measured. Blood flow was measured as described in *Diabetes* (1987) 36:43A. Albumin permeation was measured using $^{125}$I-labeled albumin according to a ratio described in *Diabetes* (1987) 36:813-821. As expected, blood flow was increased (by a factor of 1.2) and albumin permeation was increased (by a factor of 1.6) in the "diabetic" chamber as compared to the control, as shown in Table 1. The tissues marked "diabetic" were those administered the D-glucose.

TABLE 1

| | Blood Flow ml/g (wet wt)/min | Index of Albumin Permeation |
|---|---|---|
| Control | 0.18 ± 0.01* | 2.31 ± 0.12 |
| Diabetic | 0.22 ± 0.02 | 3.56 ± 0.11 |
| Diabetic + Pyruvate | 0.18 ± 0.01 | 2.45 ± 0.08 |
| Diabetic + MI | 0.19 ± 0.01 | 2.66 ± 0.14 |

*Mean ± SD

In parallel experiments, the "diabetic" chamber of the rats was simultaneously treated with either pyruvate (1 mM) or myoinositol (MI) (1 mM) along with the D-glucose. As shown in Table 1, this concomitant treatment returned blood flow to normal and markedly reduced, but did not quite normalize, albumin permeation.

EXAMPLE 2

Effect of Pyruvate on Vascular Albumin Leakage in Various Tissues

Sodium and potassium salts of pyruvate were added to a synthetic diet deficient in sodium and potassium. The final sodium content of the diet was identical to that in normal rat chow (~ −0.37%) while the potassium content was increased to ~6% of the weight of the final diet (versus ~1.1% in a normal diet). Four groups of rats were investigated: Group 1—control rats on a normal diet; Group 2—control rats fed a pyruvate-enriched diet; Group 3—diabetic rats on a normal diet; and Group 4—diabetic rats given a pyruvate-enriched diet.

Diabetes was induced by injection of streptozotocin (65 mg/kg) and the pyruvate diets were initiated the following day. Three to four weeks later blood flow was assessed by injection of 15 um $^{46}$Sc-microspheres, and vascular albumin permeation by $^{131}$I-BSA clearance was assessed in ocular tissues, sciatic nerve, kidney, aorta, and selected other tissues. Glomerular filtration rate was assessed by plasma clearance of $^{57}$Co-EDTA.

Table 2 gives the results for Groups 1, 3, and 4 above. The results show that in diabetic rats given high pyruvate diets, complete normalization of diabetes-induced increases in $^{131}$I-BSA clearance was achieved in the anterior uvea and in granulation tissue. $^{131}$I-BSA clearance was markedly reduced but not completely normalized in the choroid, sciatic nerve, aorta, diaphragm, and cecum. Albumin clearance in the retina was unaffected.

TABLE 2

Effects of Pyruvate Added to the Diet (~15% by Weight, ~18% of Total Calories) on Diabetes-Induced Increases in Vascular Plasma Clearance of $^{131}$I-BSA (ug plasma/g tissue/min).

| | Group 1 Control | Group 3 Diabetic + Normal Diet | Group 4 Diabetic + Pyruvate Diet |
|---|---|---|---|
| (Number of Rats) | (6) | (6) | (8) |
| Ocular Tissues | | | |
| Anterior Uvea | 360 ± 88* | 611 ± 113 | 339 ± 106 |
| Choroid | 230 ± 75 | 580 ± 101 | 378 ± 112 |
| Retina | 55 ± 28 | 146 ± 46 | 139 ± 44 |
| Sciatic Nerve | 59 ± 19 | 218 ± 48 | 110 ± 46 |
| Aorta | 77 ± 35 | 384 ± 50 | 212 ± 97 |
| Diaphragm | 37 ± 25 | 228 ± 104 | 145 ± 83 |
| Granulation Tissue | 55 ± 22 | 122 ± 22 | 51 ± 17 |
| Muscle | 47 ± 27 | 33 ± 12 | 36 ± 15 |
| Cecum | 173 ± 89 | 602 ± 144 | 262 ± 81 |
| Heart | 341 ± 69 | 293 ± 108 | 305 ± 99 |
| Kidney | 4949 ± 598 | 6205 ± 1675 | 5736 ± 1789 |

*Mean ± SD
ug plasma/kidney/min

EXAMPLE 3

In Vitro Assay Using Red Blood Cells

Figure 2:
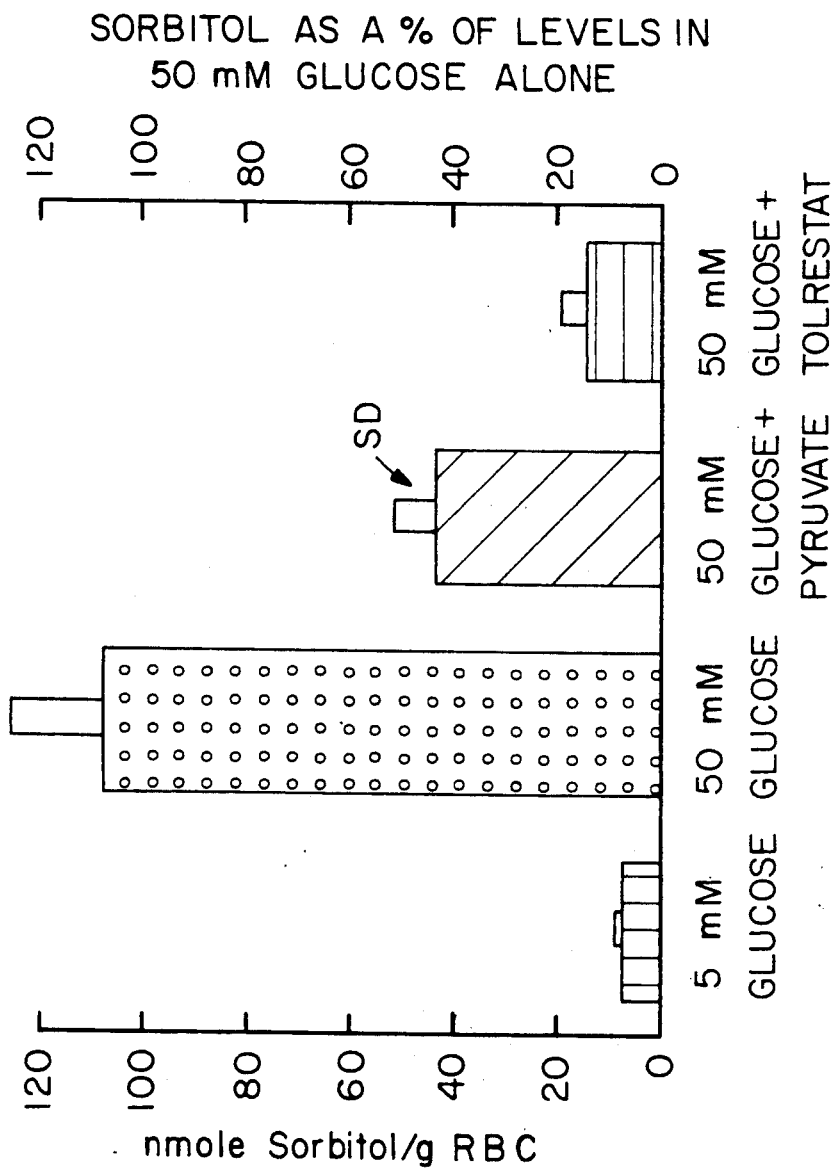
FIG. 2 shows the effect of pyruvate on sorbitol levels of red blood cells in the presence of high glucose concentration.

In order to assess the effects of pyruvate on sorbitol accumulation in red cells, we have incubated human erythrocytes in vitro with 5 to 50 mM glucose ±1 mM pyruvate for 24 hours. As shown in FIG. 2, the addition of pyruvate reduced sorbitol levels (measured by gas chromatography/mass spectrometry) by more than 50%; Tolrestat, an inhibitor of aldose reductase, reduced sorbitol levels by ~85%.

EXAMPLE 4

Formulations

The following are exemplary formulations for the administration of pyruvate and niacin.

Formulation A: Eight ounces orange juice is added to 10 g calcium pyruvate and thoroughly mixed.

Formulation B: One g niacin is mixed with one packet instant cocoa mix. The mixture is then dissolved in hot water.

Formulation C: Five g of calcium pyruvate is crushed into a bouillon cube and the crushed material dissolved in hot water.

Formulation D: Ten g of microencapsulated pyruvate potassium and calcium salts are mixed with eight ounces of tomato juice.

I claim:

1. A method to ameliorate or reduce vascular albumin leakage induced by diabetes in diabetic subjects, which method comprises administering to said diabetic subjects pyruvic acid or its pharmaceutically acceptable salts in an amount effective to ameliorate or reduce said vascular albumin leakage.

2. The method of claim 1 wherein the salt is selected from the sodium, potassium, and calcium salts.

3. The method of claim 1 wherein said administering is followed by at least one additional administration of said pyruvic acid or salt thereof.

4. The method of claim 1 wherein the effective amount is 10-100 g of pyruvate per day.

5. The method of claim 1 wherein the pyruvic acid or salt thereof is administered as a dietary supplement.

* * * * *